United States Patent [19]
Bernerd et al.

[11] Patent Number: 6,079,415
[45] Date of Patent: Jun. 27, 2000

[54] PROCESS FOR EVALUATING THE DAMAGE INDUCED IN SKIN BY UV-A RADIATION

[75] Inventors: Françoise Bernerd, Paris; Daniel Asselineau, Antony, both of France

[73] Assignee: Societe L'Oreal S.A., Paris, France

[21] Appl. No.: 08/997,256

[22] Filed: Dec. 23, 1997

[30] Foreign Application Priority Data

Dec. 24, 1996 [FR] France .................................. 96 15987

[51] Int. Cl.$^7$ ................................................. A61B 19/00
[52] U.S. Cl. ............................................. 128/898; 436/63
[58] Field of Search ........................... 128/898; 600/309, 600/310; 604/19, 20; 436/63

[56] References Cited

U.S. PATENT DOCUMENTS 3,967,124  6/1976  Strutz .

FOREIGN PATENT DOCUMENTS

| 0358506 | 3/1990 | European Pat. Off. . |
| 2689904 | 10/1993 | France . |
| 91/16010 | 10/1991 | WIPO . |

*Primary Examiner*—Mickey Yu
*Assistant Examiner*—Kelly O'Hara
*Attorney, Agent, or Firm*—Burns, Doane, Swecker & Mathis, L.L.P.

[57] ABSTRACT

A process for evaluating the type A ultraviolet radiation induced damage to the skin and/or the dermis. The invention also relates to a method of evaluating substances capable of modulating the damage induced in the skin and/or dermis by type A ultraviolet radiation.

17 Claims, 2 Drawing Sheets

PROCESS FOR EVALUATING THE DAMAGE INDUCED IN SKIN BY UV-A RADIATION

BACKGROUND OF THE INVENTION

1. Technical Field of the Invention

The present invention relates to a process for evaluating the damage induced in the skin and/or the damage caused by type A ultraviolet radiation.

2. Description of the Prior Art

Solar radiation is composed, inter alia, of type A ultraviolet radiation with wavelengths ranging from 320 nm to 400 nm (UV-A) and type B ultraviolet radiation has wavelengths ranging from 280 to 320 nm (UV-B).

U-B radiation is highly energetic and poorly penetrating. It is not represented to a significant extent in sunlight, but is dependent on climatic variations (cloudy and overcast weather and the like). The presence of UV-B radiation also varies according to the time of day (i.e., notion of peak (zenith)).

UV-A radiation is less energetic than UV-B radiation, but more penetrating and it is present in a greater amount in sunlight (at least 100 times more UV-A than UV-B). UV-A radiation is also less dependent on climatic variations and is present regardless of the time of day.

It is known that solar radiation is responsible for certain beneficial effects on the skin, such as, for example, skin darkening or tanning, but it is also capable of inducing damage in the skin, particularly in the case of so-called "sensitive" skin or of skin continuously exposed to sunlight.

In terms of beneficial effects or advantages, darkening of the skin, commonly called tanning, is an essential element in the skin's system of defense. Indeed, in response to ultraviolet radiation, the melanocytes of the top layer of the epidermis synthesize melanin which, once incorporated into the keratinocytes, act as a screening agent which is situated on the surface of the skin. The screening agent absorbs ultraviolet radiation. The purpose of the absorption is to reduce the quantity of ultraviolet radiation which crosses the skin layers in order to prevent the ultraviolet radiation from reaching the deep layers of the skin and thereby causing damage to the skin.

With respect to the harmful effects of ultraviolet radiation, it is known that excessive exposure of the skin to ultraviolet radiation, especially solar radiation, can lead to a change in the elasticity of the skin, and in the content of certain compounds within the skin, and thus promote the acceleration of the natural skin aging process. This accelerated or premature aging process due to UV radiation is generally called photoaging or actinic aging or dermatoheliosis.

Photoaging therefore results from the action of extrinsic factors on the skin, including solar radiation and, in particular, UV rays.

Photoaging is the consequence of the repetition of defined events, induced by these extrinsic factors, in particular, solar radiation, which defined events have up until now been assumed but never demonstrated.

Defined events are understood to mean any single or isolated event resulting from irradiation by UV radiation.

In man, photoaging causes the skin to have a dry, rough clinical appearance associated with a loss of elasticity, as well as marked wrinkles.

The histological signs of photoaging are (for a review, Gilchrest B. A., *Skin and Aging Processes,* 1989, CRC Press) at the epidermal level: the variation in the thickness of the epidermis (atrophy or hyperplasia according to the zones observed), a cellular atypia (Kligman L. M. and Kligman A. M., *Photodermatol.,* 1986, 3: 215–227), a loss of cell polarity, an unevenness of the horny layer, a reduction in the number of Langerhans' cells (Lavker R. M. et al., *J. Invest. Dermatol.,* 1987, 88: 44s–51s), a pigmentation characterized by a mosaic appearance with hypo- or hyperpigmentation zones, and a linearization of the dermoepidermal junction (Lavker R. M., *J. Invest. Dermatol.,* 1979, 73: 59-).

The epidermal impairments are in fact relatively minor compared with the dermal impairments which are the most obvious and the most substantial (Kligman L. M. and Kligman A. M., *Photodermatol.,* 1986, 3: 215–227).

It is indeed at the level of the extracellular matrix that the principal effects are observed. The fibroblasts are hyperactive (Kligman L. M. and Kligman A. M., *Photodermatol.,* 1986, 3: 215–227). The collagen is reduced in quantity (Oikarinen A. et al., *Photodermatol.,* 1985, 2: 15–26, Warren R. et al., *J. Am. Acad. Dermatol.,* 1991, 25: 751–760). The solubility of the fibers is reduced (Oikarinen A. and Kallioinen M., *Photodermatol.,* 1989, 6: 24–31), and a basophilic degeneration is observed.

The ultrastructural impairments of collagen result in a decrease in the number of fibrils, a reduction in the electron density, a reduction in the transverse striations (Mitchell R. E., *J. Invest. Dermatol.,* 1967, 48: 203–220). Conversely, the elastic tissue undergoes hyperplasia (Kligman A. M., *J.A.M.A.,* 1969, 210: 2377–2380, Warren R. et al., *J. Am. Acad. Dermatol.,* 1991, 25: 751–760). The middle dermis is characterized by a regrouping of fibers, thus forming a superficial zone called "grenz zone", which fibers are absent from the papillary dermis. In the deepest part of the dermis, the elastic tissue is abnormal and disorganized (Chen V. L. et al., *J. Invest. Dermatol.,* 1986, 87: 334–337), but in particular, it is present in a large quantity, which results histologically in a mass of elastic tissue. This phenomenon is known as actinic elastosis (Braverman I. M. and Fonferko E., *J. Invest. Dermatol.,* 1982, 78: 434–443; Matsuoka L. Y. and Uitto J., *Aging and the Skin,* Balin A. K. and Kligman A. M. Eds., Raven Press N.Y. 1989, 7, 141–151). Elastin has a granular appearance (elastotic material) and inclusions in electron microscopy (Braverman I. M. and Fonferko E., *J. Invest. Dermatol.,* 1982, 78: 434–443). The glycosaminoglycans and the proteoglycans are increased (Smith J. G. et al., *J. Invest. Dermatol.,* 1962, 39: 347–350, Sams W. M. and Smith J. G., *J. Invest. Dermatol.,* 1961, 37: 447–452).

The presence of a dermal infiltrate composed of mastocytes, lymphocytes and histiocytes has often been observed (Lavker R. M. and Kligman A. M., *J. Invest. Dermatol.,* 1988, 90: 325–330). The blood vessels are also modified (Braverman I. M. and Fonferko E., *J. Invest. Dermatol.,* 1982, 78: 444–448). In particular, their number is reduced, the endothelial cells are dilated and the wall of the vessels is thickened and a lamination of the basal membrane of the endothelial cells is observed.

However, even if the clinical and histological signs of photoaged skin have been well studied, the processes which lead to these signs remain unknown to this day. In particular, the respective role of UV-A and UV-B in these processes has not been demonstrated.

This is largely due to the difficulty in using a simple and reliable study model.

Animal models developed with the aim of reproducing the damage caused by UV radiation and with a pharmacological aim to test "antiaging" molecules are known in the prior art (Sams W. M. et al., *J. Invest. Dermatol.,* 1964, 43: 467–471;

Kligman L. H., Yearly review, the hairless mouse and photoaging; *Photochem. Photobiol.,* 1991, 54(6), 1109–1118).

However, these models require the use of laboratory animals, which may present ethical problems.

Furthermore, to obtain a photoaged image which is close to what is real, it is necessary, with these models, to perform the irradiation chronically or continuously for several weeks, which makes the use of such models cumbersome.

The animals used in these models are generally mice, whose cells are different, in a number of respects, from human cells.

Furthermore, the skin of mice is much finer than human skin and this parameter should be considered when evaluating the effects of UV radiation, because these effects depend on the penetration of the rays through the skin.

The dermis of mice is different from the human dermis (papillary and cross-linked dermis does not exist in mice) and can have, depending on the species used in the model, numerous residues of degenerate hair follicles.

Finally, these models do not give any precise indications on the early events which lead to the histological image of photoaging.

Study models in man are also known (Scharffetter K. et al., *Arch. Dermatol. Res.,* 1991, 283: 506–511; Korwin-Zmijowska C. et al., *Nouv. Dermatol.,* 1993, 12: 487), but those models are difficult to use. The use of human volunteers can present ethical difficulties and unavoidably brings about constraints for the subject.

Furthermore, the variability between individuals (skin phototype, age of the subject, too much space medical history, ongoing treatments and the like) is such that the reproducibility of the results may not be achieved.

Finally, in vitro models are known. Some of these models require cell cultures in which the effects of the UV irradiation on one or more cell markers in the culture are studied.

The effects of the UV-A radiation have thus been studied on the keratinocytes (epidermal cells), the fibroblasts (cells of the dermis), Langerhans' cells (immunocompetent cells of the epidermis), or the melanocytes (pigment cells) (Gilchrest B. A., *J. Gerontol.,* 1980, 35: 537–541; Scharffetter K. et al., *Arch. Dermatol. Res.,* 1991, 283: 506–511; Petersen M. J. et al., *J. Invest. Dermatol.,* 1992, 99: 440–444; Nascimento A. et al., *Nucleic Acids Res.,* 1993, 21(5), 1103–1109).

The reason why such models cannot reflect what is really happening can be readily understood. These models are cultures of monolayer cells, which are very different from an actual tissue, especially with its three-dimensional structure. Generally, cultures are produced from a single cell population, which also does not reflect reality.

Accordingly, the influence of the thickness of the cells affected by the radiation and the role of the penetration of UV radiation into the skin, which is obviously dependent on the thickness of the cell layers which must be penetrated cannot be studied using such models.

The absence of a matrix context, particularly with respect to the dermal fibroblasts which are essential for their metabolic activity, distorts the interpretations of the results obtained; it is indeed difficult to extrapolate the data obtained on plastic in vitro for a real situation in vivo in man.

It is impossible, with this type of model, to conduct product applications or studies by the topical route of administration.

Finally, some of these models require cell lines, that is to say genetically modified cells which also cannot reflect the physiological reality of normal cells.

Models using epidermis or skin equivalents are also known. With respect to the models using epidermis equivalents, their principal disadvantage results from the fact that they do not represent what is real because of the absence of a dermis or of dermis equivalent (Noel-Hudson M. S. et al., *Nouv. Dermatol.,* 1993, 12: 493). The tanning tests developed on epidermis equivalents containing melanocytes (FR 2 689 904) may also be noted.

Other studies use skin equivalents (Mammone, et al., *J. Invest. Dermatol.,* 1992, 98(4), 655; Ridge J. M. et al., *Clin. Res.,* 1992, 40(2): 543A; Reece B. et al., *J. Soc. Cosmet. Chem.,* 1992, 43: 307–312; Pelle E. et al., *J. Invest. Dermatol.,* 1993, 100, (4), 595; Nelson D. et al., *Photochem. Photobiol.,* 1993, 57(5): 830–837; Haake and Polakowska, *Cell death and differentiation,* 1995, vol. 2, 183–193).

Independently of the model selected, which is sometimes quite different from normal skin, these studies have most often been very brief and have never studied the specific influence of UV-A radiation on markers linked to photoaging.

Accordingly, before the date of the present invention, no study model has made it possible to study and understand the events whose repetition leads to clinical and histological signs of photoaging.

The human skin consists of two compartments, namely a superficial compartment, the epidermis, and a deep compartment, the dermis.

The natural human epidermis is mainly composed of three types of cells which are the keratinocytes, which are highly predominant, the melanocytes and the Langerhans' cells. Each of these cell types contributes, through its specific functions, to the essential role played in the body by the skin.

The dermis provides a solid support to the epidermis. The dermis also its nutrient-providing component. It consists mainly of fibroblasts and an extracellular matrix itself composed mainly of collagen, elastin and of a substance (called ground substance), which components are synthesized by their fibroblasts. Leukocytes, mastocytes or tissue macrophages also exist therein. It also consists of blood vessels and nerve fibers. In normal skin, that is to say, skin which is neither pathologic nor cicatricial, the fibroblast is in a quiescent state, that is to say is nonproliferative, is not very active from a metabolic point of view and is not mobile.

The epidermis is the first target reached by solar radiation, particularly, UV radiation.

The weakly penetrating UV-B radiation reaches mainly the epidermis. The role of the UV-B radiation has been clearly demonstrated in the induction of UV-induced skin cancers. It has, in fact, as a principal chromophore, nucleic acids, in particular, deoxyribonucleic acid, in which it induces lesions and/or mutations (Eller M. S., 1995, in *Photodamage.,* 26–56, Blackwell ed.)

In contrast, the role of the UV-A radiation in the induction of the defined events whose repetition leads to the photoaging phenotype is not known, even if its high penetrating power suggests that it reaches the dermis in which it induces its damaging effects.

SUMMARY OF THE INVENTION

The inventors have been interested in the skin for a long time and, in particular, in its interaction with solar radiation. After lengthy studies, the inventors have now discovered certain specific effects from type A UV radiation in the skin, particularly in the dermis.

The inventors have been able to show that irradiation with UV-A radiation induces damage in the dermis specific to the wavelengths of UV-A radiation. Thus, they have been able to show that UV-A radiation induces the production of type I collagenase by the fibroblasts, that the number of the fibroblasts decreases dramatically when exposed to UV-A radiation with up to complete disappearance of fibroblasts within 48 hours following the irradiation at least over a dermis thickness which depends on the irradiation parameters, and that the dermis part from which the fibroblasts have disappeared is recolonized by subjacent fibroblasts not affected by the radiation. These three events are directly linked to irradiation by UV-A radiation.

It can be easily understood why the production of collagenase (an enzyme which degrades collagen) in a structure, e.g., skin, in which one of the essential elements is collagen can only lead to dramatic effects for the structure, e.g., skin.

It can also be understood why the disappearance, induced by UV-A radiation, of fibroblasts, major components of the dermis and components which regenerate it, can also result in dramatic effects for the skin.

Finally, recolonization occurs only if at least part of the fibroblasts of the dermis is not affected by the radiation. This spontaneous repair of the damage induced by radiation, while it is of a favorable nature in the sense that it corrects the damaging effects of UV radiation, is nonetheless one of the causes of the photoaging phenotype. Indeed, the fibroblasts need to have left their state of quiescence in order to be capable of recolonizing the dermal tissue. This implies that they multiply, that their metabolism has resumed and therefore that they have again started synthesizing the components of the extracellular matrix whose overaccumulation can damage the skin.

A skin which has been subjected to repeated aggression from solar radiation and particularly from its UV-A component, whose dermis has therefore been subjected to degradation, is skin which appears to age prematurely. The repetition of these phenomena causes the skin to have the characteristics of photoaged skin.

The discovery of these specific markers of the action of UV-A radiation on the skin, particularly on the dermis, has led the inventors to develop a study model which allows the evaluation of products capable of modulating and/or correcting the damage induced in the skin and particularly in the dermis by type A ultraviolet radiation.

The subject of the invention is therefore a process for evaluating the damage induced in the skin by type A ultraviolet radiation, wherein a skin equivalent obtained in vitro is subjected to at least a type A ultraviolet radiation for a sufficient time, such that the variation of a marker specific for the damage induced in the skin by the type A ultraviolet radiation is measured and the results of this measurement are evaluated relative to a control.

According to a specific feature, the subject of the invention is a process for evaluating the damage induced in skin by type A ultraviolet radiation, wherein a skin equivalent obtained in vitro is subjected to at least a type A ultraviolet radiation for a sufficient time, in that the variation of a marker specific for the damage induced in the dermis by the type A ultraviolet radiation is measured and such that the results of this measurement are evaluated relative to a control.

Figure 1A:
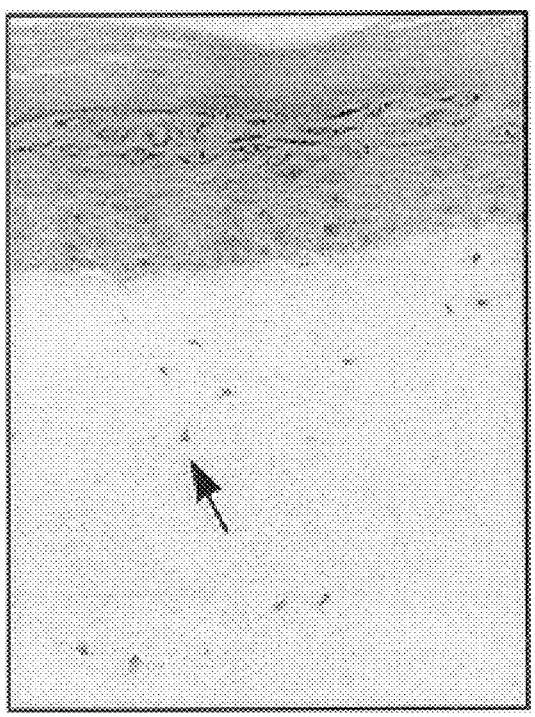
FIGS. 1a, 1b, 1c and 1d depict the conventional histology or the immunofluorescence of a dermis equivalent before and after it is exposed to UV-A irradiation.

DETAILED DESCRIPTION OF BEST MODE AND SPECIFIC/PREFERRED EMBODIMENTS OF THE INVENTION

According to the present invention, any skin equivalent which has a living dermis equivalent can be used. By the term "living dermis equivalent" is intended any dermis equivalent containing living fibroblasts. There may be mentioned in this regard, for example, the skin equivalents described in EP-0,285,471, EP-0,285,474, EP-0,418,035, WO-A-90/02796, WO-A-91/16010, EP-0,197,090, EP-020, 753, and CA-2,119,064.

Accordingly, the invention has numerous advantages linked to the three-dimensional appearance of a skin equivalent, and the presence of the two tissues (epidermis equivalent and dermis equivalent) which makes it possible to study the interactions between the two tissues and the role of each cell type in response to irradiation, to the nature and to the origin of the fibroblasts used, to the composition of the starting matrix, to the capacity to vary the thickness of the dermis equivalent, to the variable cell density of the epidermis equivalent, to the possible modification of the culture medium used to obtain the skin equivalent, and to the capacity to vary the nature, quality and quantity of radiation used.

The dermis equivalent used according to the invention may comprise, for example, mixed collagen/fibroblast lattices, subcutaneous substitutes based on collagen containing fibroblasts or on any other support compatible with cell viability in which fibroblasts could be included.

Preferably, according to the invention, the dermis equivalent consists of mixed collagen/fibroblast lattices.

The fibroblasts used according to the invention may be from any species (man, mice, and the like) and of any tissue origin (skin, lung and the like).

The fibroblasts used according to the invention can be obtained from healthy or pathological tissues.

Preferably, according to the invention, fibroblasts of normal human skin are used. However, it is conceivable for the support to comprise, in addition, other cell types and/or other types of protein, for example, glycosaminoglycans or elastin fibers.

The density of cells used according to the present invention is in general that described in the prior art in relation to the skin equivalents obtained in vitro. However, it is possible to vary this density in any proportion as long as it remains useful for the evaluation which is the object of the process of the invention.

The thickness of the dermis equivalent used according to the invention is in general that described in the prior art. It is known, according to this prior art, that this thickness depends on the quantity of collagen/cell mixture which is used. In general, this thickness ranges from 0.05 mm to several millimeters. Preferably, according to the present invention, the thickness of the dermis equivalent ranges from 0.20 mm to 1.5 mm.

It may prove advantageous to vary this thickness in any proportion judged to be useful for the evaluation which is the object of the process of the present invention. Those skilled in the art would readily understand how to adapt the quantity of collagen/cell mixture which they use in order to obtain the dermis equivalent with the desired thickness.

According to the present invention, the treated skin equivalent is subjected to type A ultraviolet radiation for a sufficient time. By "type A ultraviolet radiation" is intended any radiation having at least the characteristics of type A ultraviolet radiation, that is to say having at least a wavelength ranging from 320 nm to 400 nm.

This radiation may be solar radiation or any artificially reproduced equivalent.

Preferably, according to the invention, an artificially reproduced radiation is used which has at least a wavelength ranging from 320 nm to 400 nm, and advantageously radiation having wavelengths solely ranging from 320 nm to 400 nm. The apparatus reproducing this type of radiation is well known in the art. There may be mentioned, by way of example, the solar simulator having the trademark "IDEM 3000" by ARQUANTIEL or the solar simulator by the trade name ORIEL. Irrespective of the apparatus selected, it should be equipped with 3 mm SCHOTT WG 335 filters which eliminate wavelengths of less than 320 nm. It is also possible to use tanning lamp apparatus, such as for example the UVASUN 3000 apparatus which is used for a spectrum having wavelengths greater than 340 nm.

In this regard, the invention has the advantage of allowing the evaluation of the exact nature of the radiation emitted by equipment reproducing solar radiation, such as for example, tanning lamps. It is known that it is important, with such equipment, that certain wavelengths are not emitted so as to protect the skin from the damaging effects which they generate. The process of the invention can make it possible to perfectly characterize the radiation emitted by evaluating the damage caused by such equipment.

In general, the time during which the skin equivalent obtained in vitro, treated with UV-A type radiation, is exposed is determined both by the radiation parameters which it is desired to use, but also by the effect which it is desired to obtain. It is at least the time necessary to see the appearance of a modification of the level of expression of the marker specific for the damage induced in the dermis by the type A ultraviolet radiation.

This exposure time to radiation may range from 1 minute to a few hours. Preferably, according to the invention, the exposure time ranges from 5 to 120 minutes.

According to the invention, the variation of a marker specific for the damage induced in skin, more particularly in the dermis, by type A ultraviolet radiation is measured and the results of this measurement is evaluated relative to a control.

By "marker specific for the damage induced in skin, more particularly in the dermis, by type A ultraviolet radiation" is intended any component whose presence or absence, or the modification of whose expression or the modification of whose distribution can be measured in response to exposure to type A radiation.

Examples of typical markers include, without limitation, nucleic acids (ribonucleic or deoxyribonucleic acid), proteins or group of proteins, bound or otherwise, ions, cells, cellular membranes, cellular organelles, lipids or polysaccharides.

More particularly, according to the invention, the marker specific for the damage induced by type A ultraviolet radiation is located in the dermis.

As seen above, the inventors have been able to show that irradiation with UV-A radiation induces damage in the dermis specific to the wavelengths of UV-A radiation. Thus, the inventors have been able to show that UV-A radiation induces the production of type I collagenase by the fibroblasts, which results in an increase in its concentration in the medium. It has also been shown that the number of fibroblasts decreases dramatically because of the irradiation in the 48 hours following the irradiation, possibly up to complete disappearance, at least over a dermis thickness which depends on the irradiation parameters. Finally, it has shown that the dermis part from which the fibroblasts have disappeared is recolonized by subjacent fibroblasts not affected by the radiation.

Preferably, according to the invention, the marker specific for the damage induced in the dermis by type A ultraviolet radiation is the quantity of type I collagenase produced by the fibroblasts and/or the number of the fibroblasts in the dermis and/or the level of recolonization of the dermis by the subjacent fibroblasts.

By "level of recolonization" is intended the number of fibroblasts having recolonized the dermis area from which the fibroblasts disappeared after irradiation, and those at the end of a chosen time. This time may range from 10 to 20 days, preferably from 12 to 15 days.

The damage induced in the dermis by the type A ultraviolet radiation is thus represented by the variation in the marker specific for the induced damage which it would have been chosen to assay.

By "variation" is intended any modification of the quantity, concentration or distribution of the marker which is assayed.

For that, the process according to the invention comprises a step of assaying the marker specific for the damage induced.

Quite obviously, regardless of the embodiment of the process according to the present invention, any assay method known to persons skilled in the art can be used.

Methods for assaying proteins or nucleic acids include, without limitation, colorimetry, electrophoresis, reverse transcription and/or amplification by the polymerization reaction technique, mass spectrography, chromatography (gas or slab chromatography), immunological methods, optical or electron microscopy and all histological, histochemical and/or immunohistochemical techniques.

For example, in the case of the measurement of the production of type I collagenase by the fibroblasts, it is possible to use conventional biochemical techniques allowing the detection of type I collagenase or molecular biology techniques or alternatively immunohistochemical techniques using antibodies directed against type I collagenase. In this regard, there may be mentioned the kit having the trademark "ELISA" by AMERSHAM.

In the case of the measurement of the number of fibroblasts, optical and/or electron microscopy techniques, such as those described in Ganter and Jolles, Histochimie Normale et Pathologique [*Normal and Pathological Histochemistry*], Gauthier-Villars publishers, Paris, 1969, are particularly suitable. These techniques are used according to the most conventional protocols which are described in manuals. It is possible to use, for example, histological staining with hemalun-phloxine or immunolabelling techniques with the aid of antibodies which make it possible to reveal the fibroblasts.

The results of the assay, which represent the variation in the marker specific for the induced damage which it has been selected to assay, cannot in itself be directly exploited or interpreted. It becomes useful only when it is compared to a control. This control consists of a result of the same assay carried out under the same conditions, but in the absence of any irradiation or in the presence of irradiation with radiation having different characteristics.

Persons skilled in the art can easily determine, routinely, the nature of the control necessary for carrying out the process.

Preferably, the control corresponds to a skin equivalent which has not been subjected to any irradiation.

The process according to the invention can thus allow the evaluation of the damage induced in the skin by type A ultraviolet radiation. This is of great interest for the purpose of knowing the consequences of irradiating the skin with this type of radiation and the mechanisms by which the skin reacts to and modulates or corrects the effects of such radiation.

The process according to the invention involves a skin equivalent which, per se, is a perfectly manipulable object. By virtue of the prior art, it is known that the skin equivalent is cultured in a culture medium at the air/liquid interface. It is therefore possible to envision adding, to the culture medium, any substance whose influence on the effects of the type A ultraviolet radiation would be desirable to evaluate. This therefore mimics a systemic application of the substance.

However, since the skin equivalent exhibits an emerged epidermal surface, it is also possible to envision applying to the surface any substance whose influence on the effects of the type A ultraviolet radiation would also be desirable to evaluate. This therefore mimics a topical application of the substance.

It has been seen, moreover, that the inventors were able to demonstrate that the number of fibroblasts in the dermis decreases dramatically within 48 hours following the irradiation, possibly up to complete disappearance, at least over a dermis thickness which is dependent upon the irradiation parameters. The inventors also have demonstrated that the area of the dermis from which the fibroblasts have disappeared is recolonized by subjacent fibroblasts which were not affected by the radiation. Even if this spontaneous recolonization can damage the skin, it is nevertheless the case that, under certain circumstances, it may be preferable to promote, or even stimulate, this distribution by applying to the skin products and/or compositions selected for this type of property. It is therefore necessary, for this purpose, to have the benefit of a simple and rapid study model for evaluating such products and/or compositions.

Accordingly, the process according to the invention can, in addition, allow the evaluation of substances which may be capable of modulating the damage induced by type A ultraviolet radiation in the skin and/or the dermis. Thus, the process according to the invention comprises an additional step of treating the skin equivalent obtained in vitro with such a test product.

This step of treating with a product may occur before or after the step of irradiating the skin equivalent.

The control, in this case, may consist of a skin equivalent previously treated with a different quantity of the substance to be tested or of a skin equivalent not treated with the substance to be tested.

Preferably, the control consists of a skin equivalent not treated with the substance to be tested.

In general, the time during which the skin equivalent obtained in vitro is treated with a test product is determined by the time necessary for the equivalent to respond to the substance, that is to say the time necessary for it to produce its effect.

This treatment time may range from a few seconds to several days.

As a guide, the treatment time is generally between 5 minutes and 15 days.

By "treatment of the skin equivalent obtained in vitro" is intended the bringing of a skin equivalent obtained in vitro into contact with the substance which may be capable of modulating the damage induced by the type A ultraviolet radiation.

The modulation of the damage induced by the type A ultraviolet radiation may correspond to a reduction, or even a suppression of this damage. It may also correspond to its inhibition. In other words, these substances can be used for preventive or curative purposes.

The substance to be tested may be in any conceivable form, such as for example, an optionally pure active compound or an optionally active composition or a composition containing an optionally active compound.

In this regard, there may be mentioned for example sunscreen agents and/or compositions containing sunscreen agents. In this case, it is preferable to treat the skin equivalent by simply applying the compound or composition to the surface of the skin equivalent.

FIGS. 1 and 2 make it possible to better illustrate the invention, without however limiting its scope.

Figure 1B:
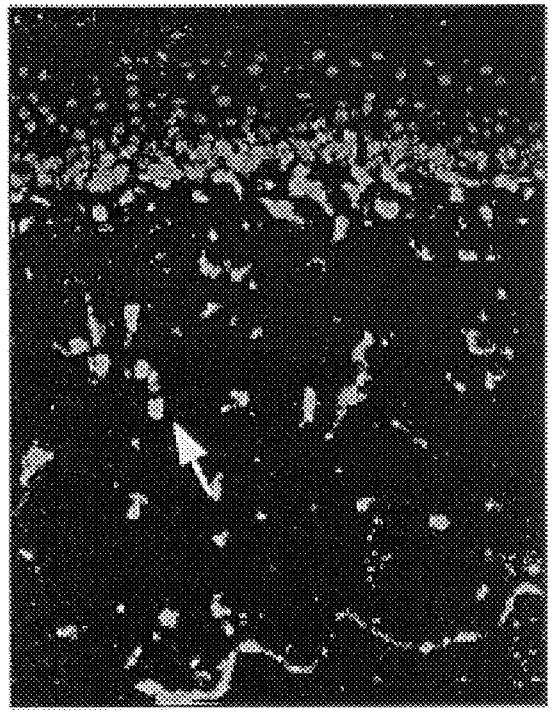
Figure 1C:
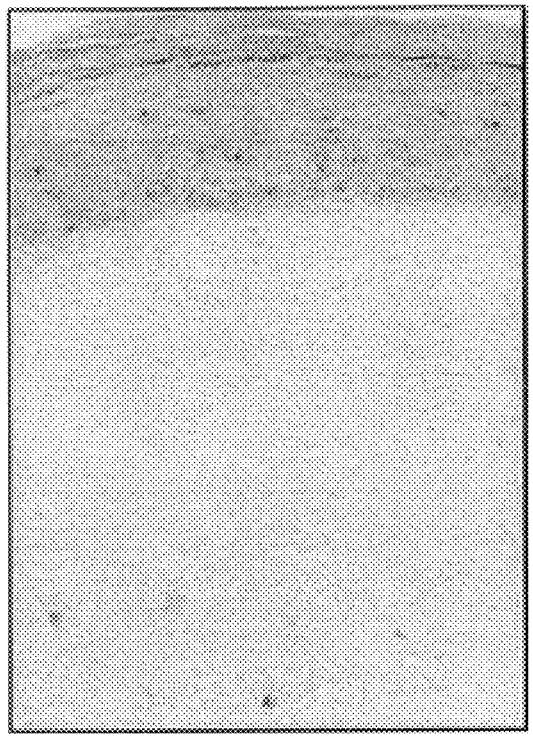
Figure 1D:

In FIG. 1, the photos show studies of sections of skin equivalents in conventional histology (FIGS. 1a and 1c) or in immunofluorescence (FIGS. 1b and 1d). FIGS. 1a and 1b correspond to a nonirradiated skin equivalent, FIGS. 1b and 1d correspond to the skin equivalent having been subjected to irradiation. The arrow visualizes the fibroblasts in the dermis equivalent.

Figure 2A:
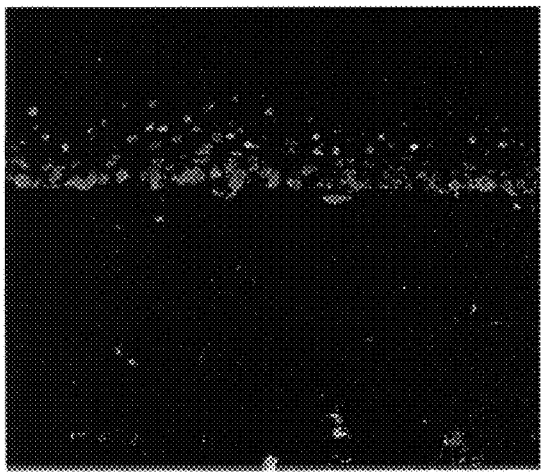
FIGS. 2a, 2b, 2c and 2d depict the conventional histology or the immunofluorescence of a dermis equivalent to which was applied 5% sunscreen.
Figure 2B:
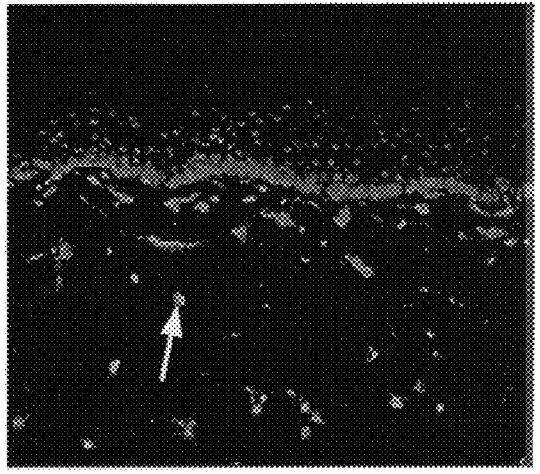

In FIG. 2, the photos show studies of sections of skin equivalents in conventional histology (FIGS. 2c and 2d) or in immunofluorescence (FIGS. 2a and 2b).

Figure 2C:
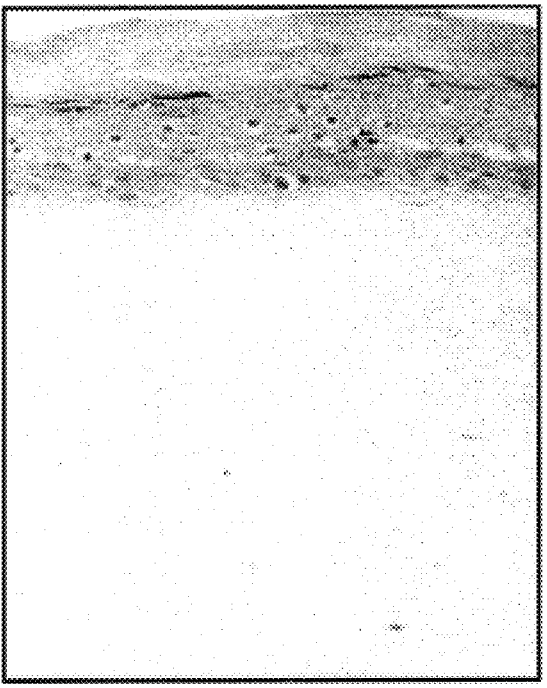
Figure 2D:
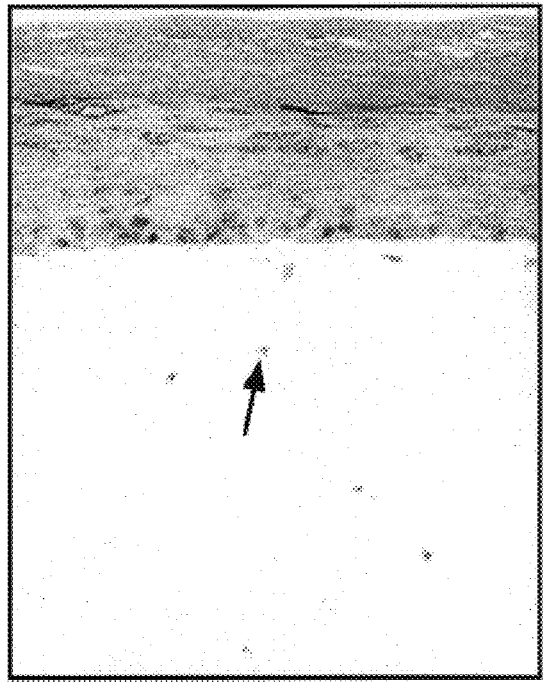

FIGS. 2a and 2c correspond to a skin equivalent previously treated with a carrier alone, then irradiated. FIGS. 2b and 2d correspond to the skin equivalent previously treated with the same carrier containing a screening agent at 5%, and then irradiated.

The arrows visualize the fibroblasts in the dermis equivalent.

The subject of the invention is also any use of the process according to the invention. It is possible to envisage, for example, the use of the process of the invention to evaluate the nature of the radiation emitted by equipment reproducing solar radiation, such as tanning lamps, and/or the damage caused by such equipment.

In order to further illustrate the present invention and the advantages thereof, the following specific examples are given, it being understood that same are intended only as illustrative and in nowise limitative.

EXAMPLE 1

Effect of type A UV radiation on the production of collagenase I

Protocol:

Skin equivalent: Samples of skin equivalents were prepared as described in Asselineau et al., *Exp. Cell. Res.*, 1985, 159, 536–539; *Models in Dermatology*, 1987, 3, 1–7. In short, the dermis equivalents were prepared as described with bovine type I collagen, fibroblasts derived from normal adult human skin in an amount of $10^6$ cells for a 7 ml gel poured in a dish 60 mm in diameter. After 3 days of contraction, the gel measured 0.240 mm in thickness. The keratinocytes (50,000) inoculated on this dermis equivalent were obtained from a mammary plasty on a woman of white race aged 35 years. The submerged culture lasted for 7 days and the culture at the air-liquid interface also 7 days. The culture medium used did not contain any phenol red. At this stage, the reconstituted skins were used.

Irradiation: The source used is a solar simulator, having the trademark "IDEM 3000" by Arquantiel, equipped with a 1000 watt Xenon lamp. A UG11/1 mm Schott filter and a 3 mm WG 335 Schott filter eliminate wavelengths of less than 320 nm. The spectrum thus obtained started at 320 nm and covered all the UV-A type radiation.

The radiance measured with the aid of an OSRAM UV-meter equipped with a UV-A probe gave a value of 20 mW/cm$^2$.

The doses delivered were 20 J/cm$^2$ and 30 J/cm$^2$.

The reconstituted skins were irradiated in the absence of culture medium and then after the time necessary for the irradiation, the reconstructed skins were placed again in an emerged culture for 48 hours.

The control consisted of an identical epidermis equivalent which was not been subjected to any irradiation (dose delivered=0 J/cm$^2$).

Assay of the interstitial collagenase (type I or MMP1):

48 hours after irradiation, the culture medium was collected and the interstitial collagenase was assayed with the aid of a kit having the trademark "Biotrack MMP-1 human ELISA system" (reference No. RPN 2610) by Amersham according to the protocol recommended by the supplier.

The results were read with the aid of a LabSystems microplate reader equipped with a 450 nm filter.

The quantity of collagenase I was calculated relative to a calibration series prepared with a standard provided with the kit, and was expressed in ng/ml.

Results and conclusion:

The table below shows that a UV-A irradiation of 20 J/cm$^2$ or of 30 J/cm$^2$ increases the quantity of interstitial collagenase assayed in the medium 48 hours after the irradiation, compared with a nonirradiated control.

|  | Dose (in J/cm$^2$) | Interstitial collagenase (in ng/ml) |
| --- | --- | --- |
| Control | 0 | 19.14 |
| Irradiated skin | 20 | 48.65 |
| Irradiated skin | 30 | 100.27 |

EXAMPLE 2

Effect of type A UV radiation on the number of fibroblasts in the dermis

A skin equivalent identical to that of Example 1 was subjected to irradiation from the same source as in Example 1 at a dose of 25 J/cm$^2$.

48 hours after the irradiation, the skin equivalent was cut in two. One half was prepared according to conventional histology techniques (Ganter and Jolles). The sections obtained were stained with hemalun, phloxine, saffron (HPS) and observed with the aid of a straight microscope in white light.

The other half was included in tissu-Tek (Miles USA) and frozen in liquid nitrogen. Sections which can be frozen were prepared and immunolabelling was performed (according to the protocol of Bernerd et al., *J. Invest. Dermatol.*, 1992, 98, 902–910) with the aid of an anti-vimentin antibody (Monosan anti-human vimentin mouse monoclonal antibody). Vimentin is an intermediate filament of the cytoskeleton of mesenchymatous cells to which the fibroblasts belong (Traub P; 1985, in: *Intermediate Filaments*; A review. Springer-Verlag, Berlin). The revealing was performed with the aid of a second anti-mouse IG antibody coupled to fluorescein. The observation was made with the aid of a fluorescence microscope.

Results and conclusion: The conventional histology (FIGS. 1a and 1c) or the immunofluorescence (FIGS. 1b and 1d) show that, 48 hours after the UV-A irradiation (25 J/cm$^2$), the fibroblasts present in the nonirradiated dermis equivalent (arrow, FIGS. 1b and 1d) have, because of their irradiation, disappeared in the superficial zone (FIGS. 1a and 1c).

EXAMPLE 3

Evaluation of the efficacy of applying sun-screening agent to the skin

Reconstructed skin: Same as for Example 1.

A skin equivalent identical to that of Example 1, previously treated, was subjected to irradiation from the same source as Example 1 at doses of 0 J/cm$^2$ and of 25 J/cm$^2$.

A carrier (water/oil emulsion) containing a cetylstearyl alcohol (80%)/oxyethylenated (33 oe) cetylstearyl alcohol and glycerol monodistearate (7%) mixture, mineral oil (15%), glycerin (20%), and water (qs), was prepared. A composition containing a sunscreen agent, Mexoryl SX (FR 82-10425), at 5%, was prepared from this carrier. The carrier or the composition containing the sunscreen in the carrier in an amount of 2 mg/cm$^2$ was applied to the surface of the skin equivalent. The samples were then irradiated as in Example 1, then the product was rinsed 3 times with sterile phosphate buffer (Seromed L 1825) and the skin equivalents were again placed in culture, at the air-liquid interface for 48 hours.

Visualization of the disappearance of the fibroblasts in the dermis equivalent: As described in Example 2.

Results and conclusion: 48 hours after the irradiation (UV-A 25 J/cm$^2$), the fibroblasts present in the dermis equivalent disappeared from the superficial zone of the dermis in the case of the skin equivalent previously treated with the carrier, which corresponds to the effects induced by UV-A radiation illustrated in Example 2 (FIGS. 2a and 2c). By comparison, in the skin equivalent previously treated with the composition containing the 5% sunscreen (FIGS. 2b and 2d), the fibroblasts did not disappear (arrow), which is evidence of protection provided by the sunscreen agent in relation to the damage induced by UV-A radiation.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for evaluating the damage induced in skin by type A ultraviolet radiation, said process comprising:

(A) obtaining an in vitro skin equivalent;
   (B) subjecting said skin equivalent to at least a type A ultraviolet radiation for a sufficient time to induce the variation of a marker specific for the damage induced in the skin by type A ultraviolet radiation;
   (C) measuring the variation of said marker; and
   (D) evaluating the results of the measurement of the variation in the marker relative to a control as a means of determining the amount of change induced by type A ultraviolet radiation.

2. The process as defined by claim 1, wherein the variation of the marker is measured for the damage induced by type A ultraviolet radiation.

3. The process as defined by claim 1, wherein the skin equivalent is an epidermis and a living dermis equivalent.

4. The process as defined by claim 1, wherein the type A ultraviolet radiation has a wavelength ranging from of at least 320 nm to 400 nm.

5. The process as defined by claim 1, wherein the time for type A ultraviolet radiation ranges from 1 minute to a few hours.

6. The process as defined by claim 5, wherein the time for the type A ultraviolet radiation ranges from 5 minutes to 120 minutes.

7. The process as defined by claim 1, wherein the marker specific for the damage induced by the type A ultraviolet radiation is selected from the group consisting of: a cell; a cell population; a nucleic acid; a protein; a group of proteins, bound or otherwise; an ion; a cellular organelle; a lipid; and a polysaccharide.

8. The process as defined by claim 1, wherein the marker specific for the damage induced by the type A ultraviolet radiation is the quantity of type I collagenase produced by the fibroblasts.

9. The process as defined by claim 1, wherein the marker specific for the damage induced by type A ultraviolet radiation is the number of fibroblasts in the dermis.

10. The process as defined by claim 1, wherein the marker specific for the damage induced by the type A ultraviolet radiation is the level of recolonization of the dermis by the subjacent fibroblasts.

11. The process as defined by claim 1, wherein the control is the same assay carried out under the same conditions, but in the absence of any irradiation or in the presence of irradiation with radiation having different characteristics.

12. The process as defined by claim 11, wherein the control is a skin equivalent which has not been subjected to any irradiation.

13. A process for evaluating the ability of a substance to modulate damage induced in the skin by type A ultraviolet radiation, said process comprising:

(A) obtaining an in vitro skin equivalent;

(B) subjecting said skin equivalent to at least a type A ultraviolet radiation for a sufficient time to induce variation of a marker specific for the damage induced in the skin by type A ultraviolet radiation;

(C) measuring the variation of said marker;

(D) evaluating the results of the measurement of the variation in the marker relative to a control;

(E) treating the skin equivalent with a substance which is to be evaluated for its ability to modulate damage to the skin caused by type A ultraviolet radiation for a sufficient time, before or after irradiating said skin equivalent; and (F) comparing the variation of the expression of said marker in said irradiated skin equivalent to the results of step D to evaluate the ability of said substance on the modulation of the damage to skin caused by type A ultraviolet radiation.

14. The process as defined by claim 13, wherein the control is a skin equivalent previously treated with a different quantity of the substance to be tested or of a skin equivalent not treated with the substance to be tested.

15. The process as defined by claim 13 wherein the control is a skin equivalent not treated with the substance to be tested.

16. The process as defined by claim 13, wherein the skin equivalent is treated for a time ranging from a few seconds to several days.

17. The process as defined by claim 13, wherein the skin equivalent is treated for a time ranging from 5 minutes to 15 days.

* * * * *